US008994921B2

(12) United States Patent
Van Boxmeer et al.

(10) Patent No.: US 8,994,921 B2
(45) Date of Patent: Mar. 31, 2015

(54) SCATTEROMETER AND LITHOGRAPHIC APPARATUS

(75) Inventors: Johan Maria Van Boxmeer, Sint Oedenrode (NL); Nicolass Antonius Allegondus Johannes Van Asten, Breda (NL); Arnold Sinke, Veldhoven (NL); Marnix Aldert Tas, Eindhoven (NL); Johannes Cornelis Maria Timmermans, Eersel (NL); Jascha Van Pommeren, Groningen (NL)

(73) Assignee: ASML Netherlands B.V., Veldhoven (NL)

( * ) Notice: Subject to any disclaimer, the term of this patent is extended or adjusted under 35 U.S.C. 154(b) by 678 days.

(21) Appl. No.: 13/126,917

(22) PCT Filed: Oct. 12, 2009

(86) PCT No.: PCT/EP2009/063270
§ 371 (c)(1),
(2), (4) Date: Jul. 8, 2011

(87) PCT Pub. No.: WO2010/052098
PCT Pub. Date: May 14, 2010

(65) Prior Publication Data
US 2011/0261339 A1   Oct. 27, 2011

Related U.S. Application Data

(60) Provisional application No. 61/112,289, filed on Nov. 7, 2008.

(51) Int. Cl.
*G03B 27/52* (2006.01)
*G03B 27/68* (2006.01)
(Continued)

(52) U.S. Cl.
CPC .......... *G03F 7/70616* (2013.01); *G01N 21/956* (2013.01)
USPC .................... 355/55; 355/52; 355/53; 355/67; 355/77

(58) Field of Classification Search
USPC ........................ 355/52, 53, 55, 67–71, 72, 77; 356/4.01–5.15, 6, 123, 237.2–237.6, 356/446, 624; 250/492.1, 492.2, 492.22, 250/548
See application file for complete search history.

(56) References Cited

U.S. PATENT DOCUMENTS 6,236,447 B1 * 5/2001 Yamada et al. ................. 355/53
7,450,225 B1 * 11/2008 Liu et al. ........................ 356/123
(Continued)

FOREIGN PATENT DOCUMENTS

EP  1 628 164 A2  2/2006
EP  1 739 493 A1  1/2007
EP  1 930 774 A1  6/2008

OTHER PUBLICATIONS

Raymond, C. J., et al., "A Scatterometric Sensor for Lithography", Proceedings of the SPIE—The International Society for Optical Engineering, Manufacturing Process Control for Microelctronic Devices and Circuits, vol. 2336, pp. 37-49 (1994).

(Continued)

*Primary Examiner* — Christina Riddle
(74) *Attorney, Agent, or Firm* — Sterne, Kessler, Goldstein & Fox P.L.L.C.

(57) ABSTRACT

A scatterometer for measuring a property of a substrate includes a focus sensing arrangement including an arrangement (65) that directs a first beam of radiation onto a focusing arrangement, to be detected by a focus sensor arrangement (61). A focus controller (67) provides control signals representative of the relative positions of the focusing arrangement (15, 69) and the substrate (W), which are required to focus the first beam of radiation on the substrate. An actuator arrangement adjusts the position of the focusing arrangement dependent on the control signals. An irradiation arrangement directs a second beam of radiation onto the substrate using the focusing arrangement, a measurement detector (18) detecting the second radiation beam after reflection from the substrate. A focus offset arrangement adjusts the focus produced by the focusing arrangement to compensate for an offset between the focusing of the first beam of radiation and the second beam of radiation.

16 Claims, 5 Drawing Sheets

(51) Int. Cl.
*G03B 27/54* (2006.01)
*G03B 27/32* (2006.01)
*G03F 7/20* (2006.01)
*G01N 21/956* (2006.01)
*G03B 27/42* (2006.01)

(56) References Cited

U.S. PATENT DOCUMENTS

| | | | |
|---|---|---|---|
| 2004/0233444 A1* | 11/2004 | Mieher et al. | 356/401 |
| 2007/0002336 A1 | 1/2007 | Pellemans et al. | |
| 2008/0135774 A1* | 6/2008 | Hugers | 250/393 |
| 2008/0151228 A1* | 6/2008 | Hugers | 356/73 |
| 2008/0259343 A1* | 10/2008 | Den Boef | 356/446 |
| 2009/0021708 A1* | 1/2009 | Boxmeer et al. | 355/44 |

OTHER PUBLICATIONS

International Search Report directed to related International Application No. PCT/EP2009/063270, mailed Jan. 29, 2010, European Patent Office, Rijswijk, Netherlands; 5 pages.

International Preliminary Report on Patentability directed to related International Application No. PCT/EP2009/063270, mailed May 10, 2011, The International Bureau of WIPO, Geneva, Switzerland; 6 pages.

* cited by examiner

SCATTEROMETER AND LITHOGRAPHIC APPARATUS

CROSS-REFERENCE TO RELATED APPLICATIONS

This application claims the benefit of U.S. provisional application 61/112,289, which was filed on Nov. 7, 2008, and which is incorporated herein in its entirety by reference.

FIELD

The present invention relates to methods of inspection usable, for example, in the manufacture of devices by lithographic techniques and to methods of manufacturing devices using lithographic techniques. In particular, the invention relates to scatterometer methods and apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

In order to measure the spectrum, the reflected beam of radiation must be focused on the scatterometer detector. As it is difficult to use the broadband radiation beam used for scatterometer measurements to determine the optimum height of an objective lens over the target to achieve the best focus, it is known to use a specialized focus sensor having its own narrowband radiation source to perform the necessary measurements. The measured value is then used to control the position of the objective lens to keep the target in optimum focus and to determine the height of fiducicials in the scatterometer which are used for references and calibrations. The inventors for the present application have realized, however, that there is a problem in such an arrangement that the best position of the objective lens as measured by the focus sensor, may not exactly match the optimum focus position for the scatterometer detector.

SUMMARY

It is desirable to provide an inspection method using a scatterometer wherein this problem is at least alleviated.

According to a first aspect of the invention, there is provided a scatterometer, configured to measure a property of a substrate, comprising:
  a focusing arrangement;
  a focus sensor;
  a focus controller responsive to said focus sensor to provide control signals effective to cause an actuator arrangement to adjust the relative positions of said focusing arrangement and the substrate which are required to focus a beam of radiation during an adjustment procedure; and
  a focus offset arrangement adapted to provide an offset to the focus produced by the focusing arrangement to compensate for differences between the focusing of said scatterometer during said adjustment procedure and the focusing of the scatterometer during use of the scatterometer.

According to a second aspect of the invention, there is provided a scatterometry method for measuring a property of a substrate using a scatterometer comprising:
  an adjustment procedure comprising:
  determining the relative positions of said focusing arrangement and the substrate which are required to focus a beam of radiation;
  providing control signals representative of said relative positions of said focusing arrangement and the substrate; and
  adjusting the relative positions of said focusing arrangement and said substrate dependent on said control signals to cause said focusing; and
  providing an offset to the focus produced by the focusing arrangement to compensate for differences between the focusing of said scatterometer during said adjustment procedure and the focusing of the scatterometer during use of the scatterometer.

According to a third aspect of the invention, there is provided a device manufacturing method comprising:
  using a lithographic apparatus to form a pattern on a substrate; and
  using a scatterometer to determine a value related to a parameter of the pattern printed by said lithography apparatus, including:
  an adjustment procedure comprising:
  determining the relative positions of said focusing arrangement and the substrate which are required to focus a beam of radiation;
  providing control signals representative of said relative positions of said focusing arrangement and the substrate; and
  adjusting the relative positions of said focusing arrangement and said substrate dependent on said control signals to cause said focusing;

and providing an offset to the focus produced by the focusing arrangement to compensate for differences between the focusing of said scatterometer during said adjustment procedure and the focusing of the scatterometer during use of the scatterometer.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
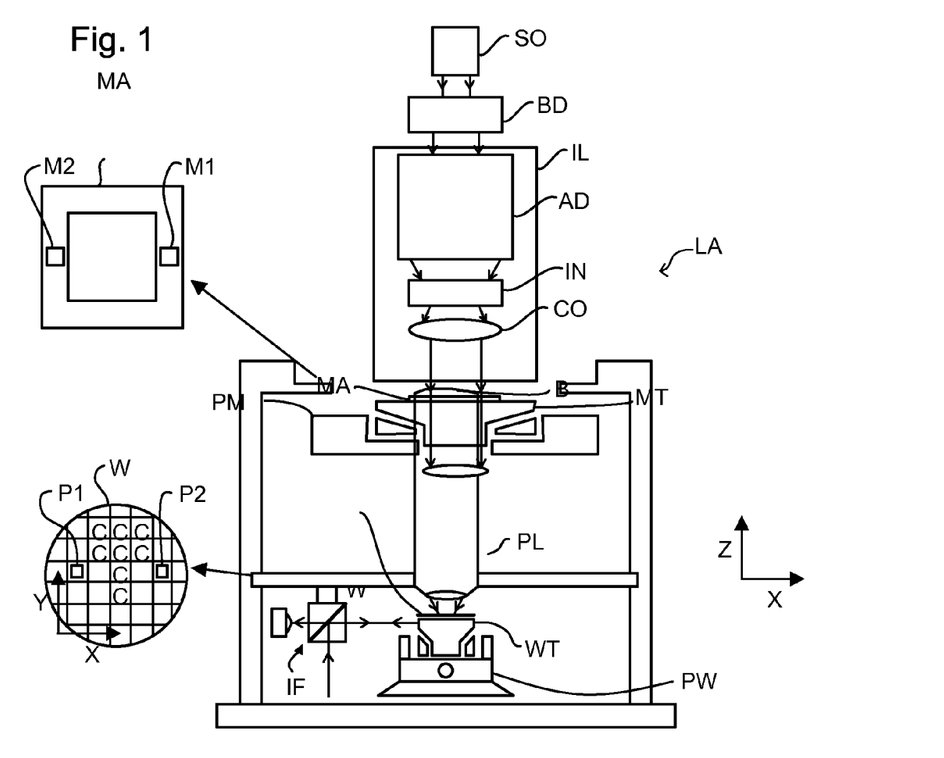
FIG. 1 depicts a lithographic apparatus.

FIG. 1 schematically depicts a lithographic apparatus. The apparatus comprises:

an illumination system (illuminator) IL configured to condition a radiation beam B (e.g. UV radiation or DUV radiation);

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device".

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
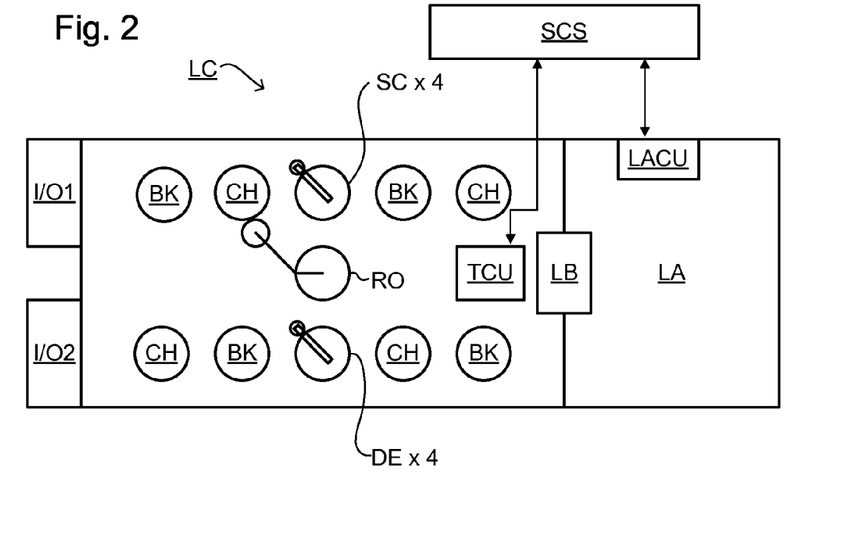
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist, which have been exposed to radiation, and those that have not—and not all inspection apparatus have sufficient sensitivity to make useful measurements of the latent image. Therefore measurements may be taken after the post-exposure bake step (PEB), which is customarily the first step, carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
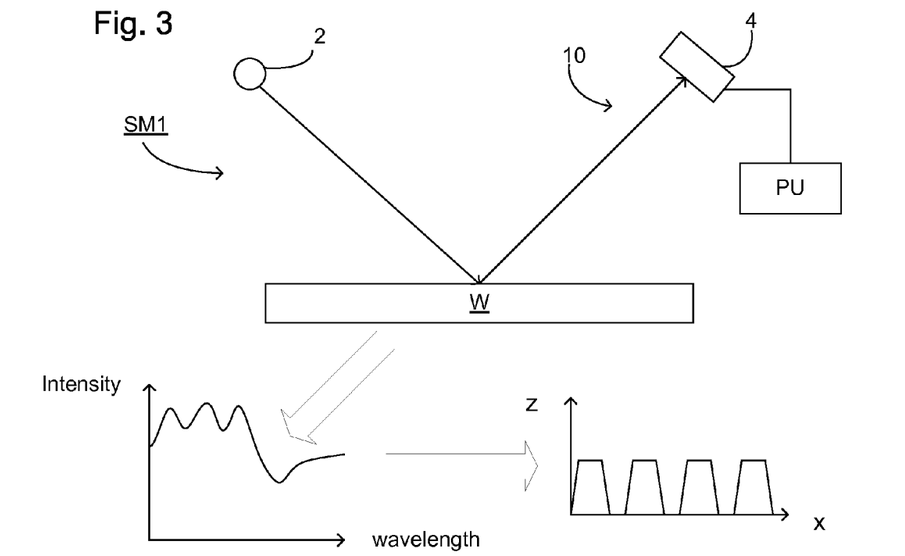
FIG. 3 depicts a first scatterometer.

FIG. 3 depicts a scatterometer that may be used in the present invention. It comprises a broadband (white light) radiation projector 2, which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
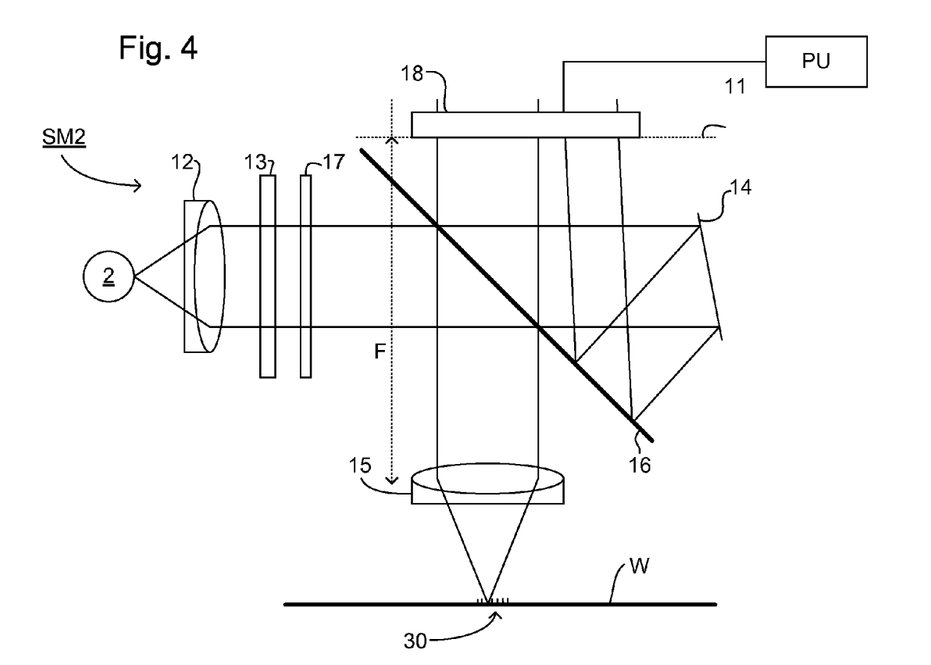
FIG. 4 depicts a second scatterometer.

Another scatterometer that may be used with the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of *8 and a spacing of at least 2*8 (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 5:
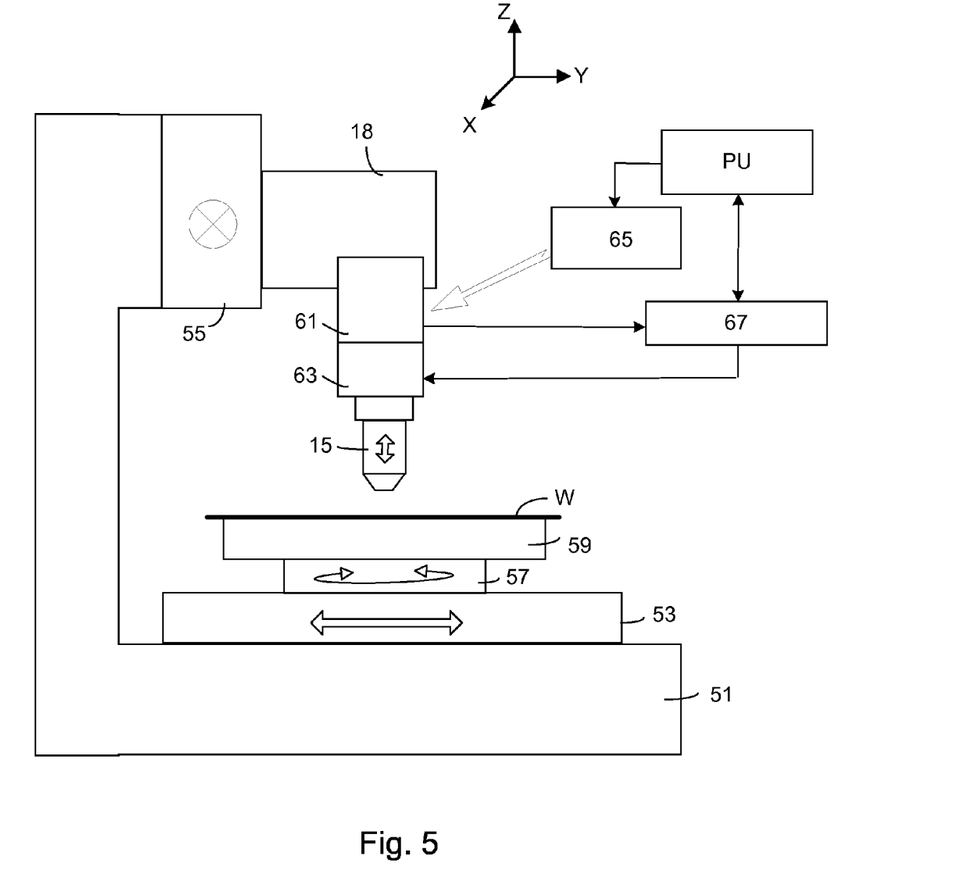
FIG. 5 depicts a third scatterometer showing details of the sensor stage and wafer table.

Referring now also to FIG. 5, this figure shows the structure of the scatterometer illustrated in FIG. 4. The scatterometer is supported by a base frame 51 which supports a linear Y stage 53 supported for movement in the direction shown by the arrow and a linear X stage 55 supported for movement in the plane of the drawing. The linear Y stage 53 carries a rotation stage 57, which in turn carries a wafer table 59 which will in use of the apparatus carry the wafer W. Supported by the linear X stage 55 so as to be movable along the X direction, there is provided the scatterometer sensor 18 indicated in FIG. 4.

In order to provide online focusing of the radiation beam on the substrate by the objective lens system 15, the scatterometer includes a focus sensing arrangement. In particular, carried by and moveable with the scatterometer sensor 18, there is provided a focus sensor 61 which in turn carries an objective stage 63 which controls the position of the objective lens system 15 indicated in FIG. 4. A focus illumination system 65 is arranged to direct a beam of radiation, indicated in the figure as an arrow, onto the focus sensor 61. This beam will pass through the objective lens system 15 onto the wafer W. A focus controller 67, under control of the processing unit PU, is effective to provide control signals to an actuator (not shown) in the objective stage 63 so as to control the movement of the objective lens arrangement in the Z direction, as indicated by the arrow in the figure, so as to focus the radiation provided by the focus illumination system onto the wafer and focus the radiation reflected by the wafer W on the wafer table 59, back onto the focus sensor 61.

However, as appreciated by the inventors, there is however a problem with the above described arrangement, that the best focus measurement measured by the focus sensor 61 does not necessarily match the best focus needed for measurements made by the scatterometer sensor 18 when measuring the spectrum of radiation reflected from the wafer in order to monitor, for example, critical dimension (CD) or overlay (OV). This may be due to the different measurement techniques used by the scatterometer sensor 18 and the focus sensor 61 due to different wavelengths in the radiation or different optical designs due to different principles such as capacitive versus optical contrast, different wafer interactions of the wafers on the wafer table 59 or different definitions of the best focus for different applications for example between CD and OV measurements. It is not possible to make further measurements by the focus sensor 61 during scatterometer measurements by the apparatus, due to time restrictions. In particular the sampling used by the focus control system will typically have a bandwidth of typically 2 KHz, that is much less than the bandwidth of the radiation used for the scatterometry measurements.

In accordance with an embodiment of the invention, the position of the focus sensor in the Z direction is adjusted during the scatterometer measurements, to compensate for the offset between the focus sensor and the focus of the scatterometry sensor 18 without needing to linearise the focus sensor.

Figure 6:
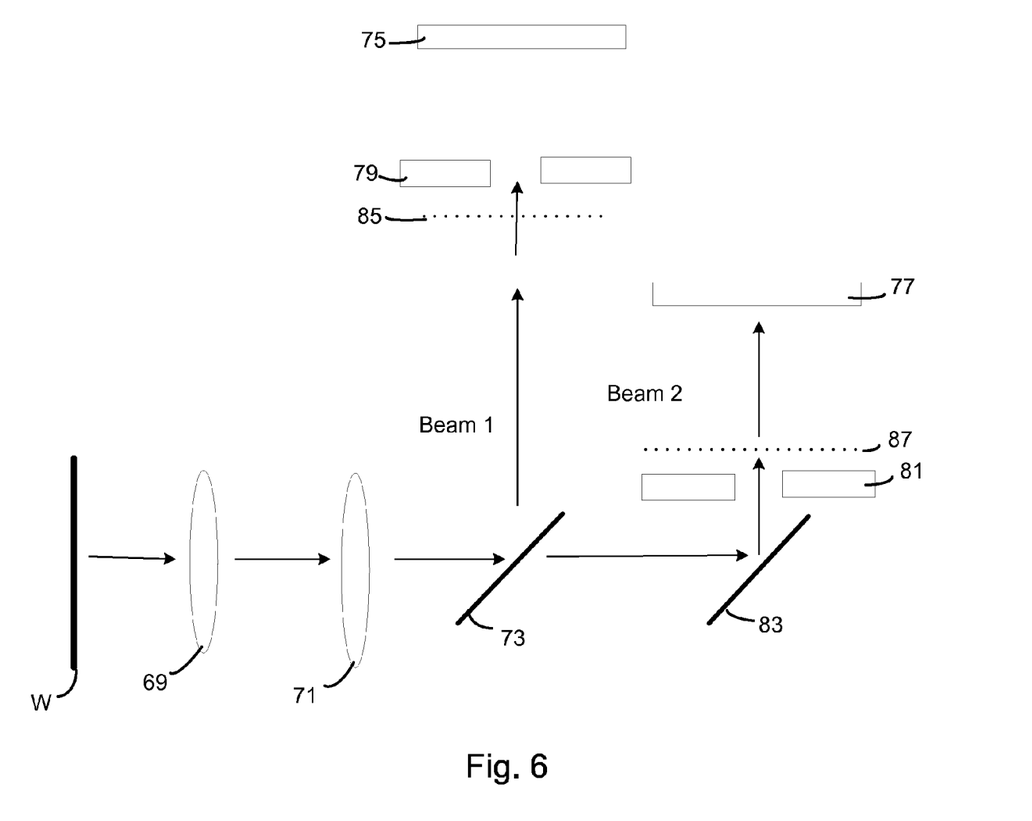
FIG. 6 depicts a schematic optical arrangement incorporated in the scatterometer shown in FIG. 5 used in a first embodiment of a scatterometer in accordance with the invention.

Referring now to FIG. 6 this figure illustrates the positions of the some of the optical components in the optical arrangement for the focus sensing arrangement generally described above, which may be used in a scatterometer in accordance with an embodiment of the invention. It will be appreciated that in FIG. 6, the wafer W is the wafer W shown in the scatterometer depicted in FIG. 5, whilst lens 69 constitutes the objective lens arrangement 15 depicted in FIG. 5, lens 71 being a focusing lens for the focus sensing arrangement. It will also be appreciated that some optical components, in particular a beam splitting arrangement for splitting radiation reflected by the wafer such that only radiation from focus illumination system 65 passes through focusing lens 71.

Radiation reflected from the wafer W passing through the lenses 69, 71, is split by mirror 73 to produce two beams, beam 1 and beam 2. Respective detectors 75 and 77 are provided to detect beam 1 and beam 2. Beam 1 passes through aperture 79 onto detector 75, whilst beam 2 passes through aperture 81 onto detector 77 after reflection from mirror 83, the detectors 75, 77, apertures 79, 81 and mirrors 73, 83 all forming part of the focus sensor 61 of FIG. 5. FIG. 6 also illustrates the position of the respective focal planes 85, 87 for each beam, beam 1 and beam 2. The optical path length between the wafer W and the focal plane 85 for the beam 1 will be equal to the optical path length between the wafer W and focal plane 87 of the beam 2. The distances between the aperture 79, 81 and the respective focal plane 85, 87 will be the same for beam 1 and beam 2.

The use of the two beams, beam 1 and beam 2 enable the sense of any deviation of the beam from the focus position on the wafer W, as well as the fact of any misfocus to be detected. In particular, at best focus, the amount of light that passes through apertures 79, 81 is equal so the outputs S1, S2 of the detectors 75, 77 is also equal. In other words, S1=S2 and S1−S2=0. If the wafer W is not at optimum focus, S1 and S2 become different and this can be detected. The position of the objective lens 69 in the objective lens arrangement 15 is then moved, using the objective stage 63 shown in FIG. 5, until S1 and S2 become equal again, the wafer W then being at best focus, with the objective lens 69 being at the best height above the wafer W for both scatterometry and alignment measurements. As explained above, in relation to the prior art, there is a problem with prior art arrangements that there may be a difference between the focus of the scatterometry sensor and the focus sensor, which may be machine, product and/or process based.

Figure 7:
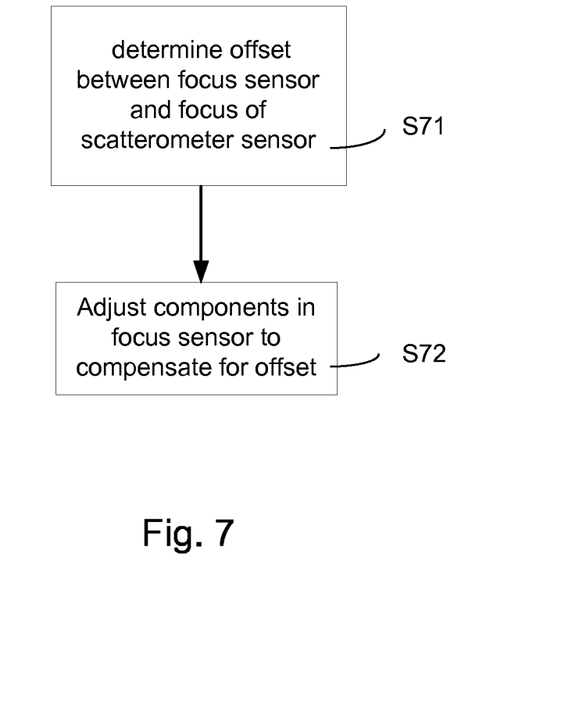
FIG. 7 is a flow diagram showing the operation of the scatterometer of FIGS. 5 and 6 according to the first embodiment of the invention.

Referring now also to FIG. 7, in accordance with the first embodiment of the invention, a reference measurement is performed offline to determine the offset between the focus as determined by the focus sensing arrangement and the focus required for a specific radiation beam used in a particular scatterometry operation. This is indicated as step S71 in FIG. 7. The offset between the focus measurements for the beam incident on the wafer W as measured by the focus sensor 61 and the scatterometer sensor 18 can be corrected in step S72 on an ongoing basis during online operation of the scatterometer, without the need to otherwise readjust the system.

The correction for the offset can be made either in the focus sensing arrangement or in the scatterometer sensor 18. In this particular embodiment, in the optical arrangement illustrated in FIG. 6, the position of the focusing lens 71 (which in prior art arrangements generally remains static) may be adjusted to change the position of the focal planes 85, 87 with respect to the respective apertures 79, 81. This position adjustment may be performed by the same actuator which adjusts the position of the objective lens 69 or by a separate actuator. In the case that the focal plane 85 is made to shift closer to the pinhole 79 in beam 1, a larger signal will be produced by detector 75, relative to that produced by detector 77. Thus S1 will be greater than S2. The difference in signals, S1−S2 can be used by controller 67 in the focus control loop, to adjust the position of the objective lens 69, which will, in turn, affect the position of the focal plane 85. The control loop will again move the objective lens 69 until S1 and S2 are equal and the focal plane 85 is back in its original position. It will be seen that by this procedure, the objective lens 69 is positioned differently relative to the wafer W compared to the absence of the application of the offset. This will affect the focus of both the scatterometer sensor 18 and the alignment function enabled by measurements made by the focus sensor 61.

Alternatively the positions of the apertures 79,81 may be adjusted. Once the offset has been corrected for, the focus controller 67 ensures by movement of the objective stage 63, that the measurements made by the detectors 75, 77 in the scatterometer sensor system 18 are taken with the corrected focus position. Whilst the focusing system detects a position of best focus, that is S1=S2, an offset is introduced for measurement systems outside the focus sensor.

Figure 8:
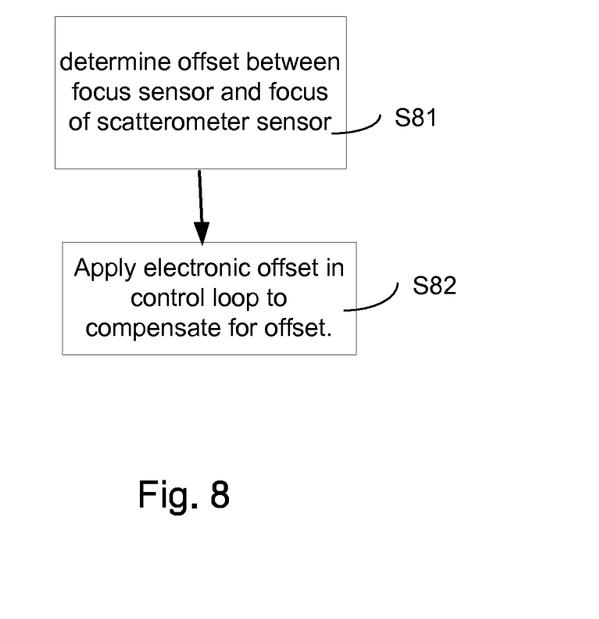
FIG. 8 is a flow diagram showing the operation of the scatterometer of FIGS. 5 and 6 according to a second embodiment of the invention.

Referring now to FIG. 8, in an alternative embodiment in accordance with the invention, instead of adjusting the optical components as in the first embodiment, a software correction can be made to the signals applied by the focus controller 67 to the actuator in the objective stage 63. As in the first embodiment, in step S 81, a reference measurement is performed offline, to determine the offset between the focus as determined by the focus sensing arrangement and the focus required for a specific radiation beam used in a particular scatterometry operation. In the subsequent online scatterometry operation, as indicated in step S 82, the focus controller 67, under the control of the processor PU, is then arranged to provide modified control signals, that is instead of making S1 and S2 equal, causing them to have a difference equal to an offset value. This is then used to control the actuator in the objective stage 63 to adjust the position of the objective lens system to the position of best focus as determined by the focus controller, taking account of the offset. It will be appreciated however, that the implementation of this embodiment requires there to be a known relationship, ideally linear, between the outputs of the focus sensor 61 and the actual linear displacement of the objective lens system. This will depend on a number of factors, including the structures of the wafer W being measured.

It will be appreciated that correction for the offset between the focus sensor and the focus of the scatterometry sensor will allow for smaller focus errors to be obtained with respect to the optimum focus, for either the scatterometer sensor 18 or the focus sensor 61, regardless of the particular application or focusing system. This will lead to a better alignment of the components of the scatterometer by the wafer positioning system described above, which will lead to more accurate CD and/or OV measurements. Furthermore a better focus for measuring the scattered radiation will also lead to more accurate CD and/or OV measurements. A better focus will lead to sharper images used for alignment of the wafer by the wafer positioning system described above, leading to smaller alignment errors. In the case of OV measurements, it will be possible to choose over the wafer where to make the measurements as the best focus will not be dependent on the wafer.

It will also be appreciated that the possibility of adjusting for the offset allows for more flexibility in the design of the focus sensor. As the sensor is not required to provide the best possible focus as it can be corrected later. Furthermore the dynamic range of the scatterometry sensor can be improved, making it possible, for example, to measure spectra produced from poorly reflective surfaces by making it possible to vary the intensity of the incident radiation. Offset correction will also make it easier to implement alternative focus sensors to the optical sensor described above, for example capacitive sensors although it will then be necessary to provide a different control system. In use of such a capacitive sensor, the optimum focus position of the objective lens is determined in an adjustment procedure, the capacitive sensor being used to determine the relative positions of the wafer W and the objective lens 69. An offset will be applied to the signals produced by the capacitive sensor to compensate for changes in measurement characteristics between the adjustment procedure and the operation of the scatterometer.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A scatterometer configured to measure a property of a substrate, comprising:
   a focusing arrangement;
   a focus sensor;
   a focus controller responsive to said focus sensor to provide control signals effective to cause an actuator arrangement to adjust relative positions of said focusing arrangement and the substrate Which are used to focus a beam of radiation during an adjustment procedure; and
   a focus offset arrangement adapted to provide an offset to the focus produced by the focusing arrangement to compensate for differences between the focusing of said scatterometer during said adjustment procedure and the focusing of the scatterometer during use of the scatterometer.

2. The scatterometer according to claim 1, comprising:
   an arrangement effective to direct a beam of radiation through said focusing arrangement onto said substrate;
   wherein said focus sensor is adapted to detect said beam of radiation after reflection from said substrate; and
   said focus offset arrangement is adapted to provide an offset to the focus produced by the focusing arrangement to compensate for differences between the focusing of said beam of radiation and the focusing of the scatterometer during use of the scatterometer.

3. The scatterometer according to claim 2, wherein the focus offset arrangement comprises:
   an arrangement effective to change the optical path length within said focusing arrangement.

4. The scatterometer according to claim 3, wherein the arrangement effective to change the optical path length comprises: a lens arrangement interposed between said focusing arrangement and said substrate; and an actuator arrangement effective to move said lens arrangement so as to vary the position at which said beam of radiation is focused after reflection at said substrate.

5. The scatterometer according to claim 4, in which the same actuator arrangement is arranged to move said lens arrangement and said focusing arrangement.

6. The scatterometer according to claim 4, in which different respective actuators are provided to move said lens arrangement and said focusing arrangement.

7. The scatterometer according to claim 1, wherein the focus offset arrangement comprises: an arrangement effective to change said control signals dependent on said offset.

8. The scatterometer according to claim 1, wherein said focus sensor is a capacitive sensor.

9. A scatterometry method for measuring a property of a substrate using a scatterometer comprising:

an adjustment procedure comprising:
  determining the relative positions of said focusing arrangement and the substrate which are required to focus a beam of radiation;
  providing control signals representative of said relative positions of said focusing arrangement and the substrate; and
  adjusting the relative positions of said focusing arrangement and said substrate dependent on said control signals to cause said focusing; and
providing an offset to the focus produced by the focusing arrangement to compensate for differences between the focusing of said scatterometer during said adjustment procedure and the focusing of the scatterometer during use of the scatterometer.

10. The method according to claim 9, comprising:
directing a beam of radiation through said focusing arrangement onto said substrate;
detecting said beam of radiation after reflection from said substrate; and
providing an offset to the focus produced by the focusing arrangement to compensate for differences between the focusing of said beam of radiation and the focusing of the scatterometer during use of the scatterometer.

11. The method according to claim 10, wherein providing the focus offset comprises: changing the optical path length within at least one of an arrangement for performing said focus sensing and an arrangement for performing said measurement detection.

12. The method according to claim 10, wherein providing the focus offset comprises:
changing said control signals dependent on said offset.

13. The method according to claim 10, wherein said focusing step is initially performed prior to said scatterometry step to provide a value for said offset to be used in subsequent scatterometry steps.

14. A lithographic apparatus comprising:
an illumination optical system arranged to illuminate a pattern;
a projection optical system arranged to project an image of the pattern on to a substrate; and
a scatterometer comprising,
  a focusing arrangement;
  a focus sensor;
  a focus controller responsive to said focus sensor to provide control signals effective to cause an actuator arrangement to adjust relative positions of said focusing arrangement and the substrate which are used to focus a beam of radiation during an adjustment procedure; and
  a focus offset arrangement adapted to provide an offset to the focus produced by the focusing arrangement to compensate for differences between the focusing of said scatterometer during said adjustment procedure and the focusing of the scatterometer during use of the scatterometer.

15. A lithographic cell comprising:
a coater arranged to coat substrates with a radiation sensitive layer;
a lithographic apparatus arranged to expose images onto the radiation sensitive layer of substrates coated by the coater:
a developer arranged to develop images exposed by the lithographic apparatus; and
a scatterometer comprising,
  a focusing arrangement;
  a focus sensor;
  a focus controller responsive to said focus sensor to provide control signals effective to cause an actuator arrangement to adjust relative positions of said focusing arrangement and the substrate which are used to focus a beam of radiation during an adjustment procedure; and
  a focus offset arrangement adapted to provide an offset to the focus produced by the focusing arrangement to compensate for differences between the focusing of said scatterometer during said adjustment procedure and the focusing of the scatterometer during use of the scatterometer.

16. A device manufacturing method comprising:
using a lithographic apparatus to form a pattern on a substrate; and
using a scatterometer to determine a value related to a parameter of the pattern printed by said lithography apparatus, including:
  an adjustment procedure comprising: determining the relative positions of said focusing arrangement and the substrate which are required to focus a beam of radiation; providing control signals representative of said relative positions of said focusing arrangement and the substrate; and
  adjusting the relative positions of said focusing arrangement and said substrate dependent on said control signals to cause said focusing; and
providing an offset to the focus produced by the focusing arrangement to compensate for differences between the focusing of said scatterometer during said adjustment procedure and the focusing of the scatterometer during use of the scatterometer.

* * * * *

UNITED STATES PATENT AND TRADEMARK OFFICE
CERTIFICATE OF CORRECTION

PATENT NO. : 8,994,921 B2  Page 1 of 1
APPLICATION NO. : 13/126917
DATED : March 31, 2015
INVENTOR(S) : Van Boxmeer et al.

It is certified that error appears in the above-identified patent and that said Letters Patent is hereby corrected as shown below:

IN THE CLAIMS

In column 12, line 26, claim 1, after "substrate", please delete "Which" and insert --which--.
In column 14, line 12, claim 15, please delete ":" and insert --;--.

Signed and Sealed this
Tenth Day of November, 2015

Michelle K. Lee
*Director of the United States Patent and Trademark Office*